(12) United States Patent
Brandt et al.

(10) Patent No.: US 11,833,348 B2
(45) Date of Patent: Dec. 5, 2023

(54) ELECTRODE LEADS HAVING MULTI-APPLICATION HELICAL NERVE CUFFS AND ASSOCIATED SYSTEMS AND METHODS

(71) Applicant: The Alfred E. Mann Foundation for Scientific Research, Valencia, CA (US)

(72) Inventors: William Andrew Brandt, Castaic, CA (US); Brian Ralph Dearden, Pasadena, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 57 days.

(21) Appl. No.: 17/463,630

(22) Filed: Sep. 1, 2021

(65) Prior Publication Data

US 2023/0010510 A1    Jan. 12, 2023

Related U.S. Application Data

(60) Provisional application No. 63/220,007, filed on Jul. 9, 2021.

(51) Int. Cl.
*A61N 1/05* (2006.01)
*A61N 1/36* (2006.01)

(52) U.S. Cl.
CPC .......... *A61N 1/0556* (2013.01); *A61N 1/3611* (2013.01)

(58) Field of Classification Search
None
See application file for complete search history.

(56) References Cited

U.S. PATENT DOCUMENTS

| | | |
|---|---|---|
| 4,573,481 A | 3/1986 | Bullara |
| 4,602,624 A | 7/1986 | Naples et al. |
| 4,940,065 A | 7/1990 | Tanagho et al. |
| 5,251,634 A | 10/1993 | Weinberg |
| 5,400,784 A | 3/1995 | Durand et al. |
| 5,439,485 A | 8/1995 | Mar et al. |
| 5,487,756 A | 1/1996 | Kallesoe et al. |
| 5,634,462 A | 6/1997 | Tyler et al. |
| 5,919,220 A | 7/1999 | Stieglitz et al. |
| 6,066,165 A | 5/2000 | Racz |
| 6,210,339 B1 | 4/2001 | Kiepen et al. |
| 6,292,703 B1 | 9/2001 | Meier et al. |
| 7,383,090 B2 | 6/2008 | O'Brien et al. |
| 7,794,256 B1 | 9/2010 | Sochor |
| 7,809,442 B2 | 10/2010 | Bolea et al. |

(Continued)

FOREIGN PATENT DOCUMENTS

WO    WO 2008092246 A1    8/2008
WO    WO 2009045772 A1    4/2009
(Continued)

OTHER PUBLICATIONS

U.S. Appl. No. 17/463,630, filed Sep. 1, 2021.
(Continued)

*Primary Examiner* — Catherine M Voorhees
*Assistant Examiner* — Elizabeth K So
(74) *Attorney, Agent, or Firm* — Henricks Slavin LLP (57) ABSTRACT

An electrode that includes an elongate lead body and a nerve cuff. The nerve cuff may include a biologically compatible, elastic, electrically insulative helical cuff body configured to be disposed around a nerve, and a plurality of electrically conductive contacts carried by the helical cuff body that are spaced from one another.

19 Claims, 10 Drawing Sheets

(56) References Cited

U.S. PATENT DOCUMENTS

| | | |
|---|---|---|
| 8,116,882 B2 | 2/2012 | Kowalczewski |
| 8,155,757 B1 | 4/2012 | Neisz et al. |
| 8,224,449 B2 | 7/2012 | Carbunaru et al. |
| 8,311,645 B2 | 11/2012 | Bolea et al. |
| 8,340,785 B2 | 12/2012 | Bonde et al. |
| 8,660,665 B2 | 2/2014 | Walter et al. |
| 8,792,973 B2 | 7/2014 | Moran et al. |
| 8,934,992 B2 | 1/2015 | Johnson et al. |
| 9,186,511 B2 | 11/2015 | Bolea |
| 9,227,053 B2 | 1/2016 | Bonde et al. |
| 9,549,708 B2 | 1/2017 | Mercanzini et al. |
| 9,603,538 B2 | 3/2017 | Fisher et al. |
| 9,849,288 B2 | 12/2017 | Meadows et al. |
| 9,889,304 B2 | 2/2018 | Mercanzini |
| 9,931,045 B2 | 4/2018 | Brunnett et al. |
| 10,758,723 B2 | 9/2020 | Fang et al. |
| 2002/0198582 A1 | 12/2002 | Edell et al. |
| 2005/0070982 A1 | 3/2005 | Heruth et al. |
| 2005/0186829 A1 | 8/2005 | Balsells |
| 2006/0030919 A1 | 2/2006 | Mrva et al. |
| 2007/0123765 A1 | 5/2007 | Hetke et al. |
| 2008/0082137 A1 | 4/2008 | Kieval et al. |
| 2008/0092246 A1 | 4/2008 | Shintani |
| 2009/0045772 A1 | 2/2009 | Cook et al. |
| 2009/0132042 A1 | 5/2009 | Hetke et al. |
| 2009/0210042 A1 | 8/2009 | Kowalczewski |
| 2010/0305674 A1 | 12/2010 | Zarembo et al. |
| 2010/0331933 A1 | 12/2010 | Carbunaru et al. |
| 2011/0066196 A1 | 3/2011 | Alexander et al. |
| 2011/0130815 A1 | 6/2011 | Gibson et al. |
| 2011/0154655 A1 | 6/2011 | Hetke et al. |
| 2011/0251473 A1 | 10/2011 | Moran et al. |
| 2011/0301665 A1 | 12/2011 | Mercanzini et al. |
| 2012/0150255 A1 | 6/2012 | Lindenthaler et al. |
| 2012/0154256 A1 | 6/2012 | Grover et al. |
| 2012/0316417 A1 | 12/2012 | Vetter |
| 2013/0030352 A1 | 1/2013 | Seymour et al. |
| 2013/0085361 A1 | 4/2013 | Mercanzini et al. |
| 2013/0090711 A1 | 4/2013 | Ramachandran et al. |
| 2013/0150938 A1 | 6/2013 | Carbunaru et al. |
| 2013/0304174 A1 | 11/2013 | Langhals et al. |
| 2014/0005763 A1 | 1/2014 | Cederna et al. |
| 2014/0058482 A1 | 2/2014 | Gupta et al. |
| 2014/0163659 A1 | 6/2014 | Boling |
| 2014/0188202 A1 | 7/2014 | Zarembo et al. |
| 2014/0228905 A1 | 8/2014 | Bolea |
| 2014/0303703 A1 | 10/2014 | Mercanzini et al. |
| 2015/0119673 A1 | 4/2015 | Pellinen et al. |
| 2015/0128413 A1 | 5/2015 | Vetter et al. |
| 2015/0157854 A1 | 6/2015 | Hetke et al. |
| 2015/0174396 A1 | 6/2015 | Fisher et al. |
| 2015/0224307 A1 | 8/2015 | Bolea |
| 2015/0374975 A1 | 12/2015 | Callegari et al. |
| 2016/0184581 A1 | 6/2016 | Bonde et al. |
| 2016/0199637 A1 | 7/2016 | Xu et al. |
| 2016/0287863 A1 | 10/2016 | Mercanzini et al. |
| 2016/0331326 A1 | 11/2016 | Xiang et al. |
| 2016/0331994 A1 | 11/2016 | Smith et al. |
| 2017/0266436 A1 | 9/2017 | Suwito et al. |
| 2018/0117313 A1 | 5/2018 | Schmidt et al. |
| 2018/0221660 A1 | 8/2018 | Suri et al. |
| 2018/0318577 A1 | 11/2018 | Ng et al. |
| 2018/0318578 A1 | 11/2018 | Ng et al. |
| 2019/0060646 A1 | 2/2019 | Ng et al. |
| 2019/0282805 A1 | 9/2019 | Schmidt et al. |
| 2020/0069935 A1 | 3/2020 | Johnson et al. |
| 2020/0083922 A1 | 3/2020 | Hong et al. |
| 2020/0146583 A1 | 5/2020 | Hestad et al. |
| 2020/0230412 A1 | 7/2020 | Rondoni et al. |
| 2020/0306526 A1 | 10/2020 | Doguet et al. |
| 2021/0205662 A1 | 7/2021 | Lu et al. |
| 2022/0062629 A1 | 3/2022 | Dearden |
| 2022/0088374 A1 | 3/2022 | Ackermann et al. |
| 2022/0313987 A1 | 10/2022 | Jenny et al. |

FOREIGN PATENT DOCUMENTS

| | | |
|---|---|---|
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |

OTHER PUBLICATIONS

U.S. Appl. No. 17/683,598, filed Mar. 1, 2022.
PCT International Search and Written Opinion dated Mar. 28, 2022 for PCT App. Ser. No. PCT/US2021/048585.
U.S. Appl. No. 17/463,611, filed Sep. 1, 2021, 20220062629 A1.
U.S. Appl. No. 17/463,630, filed Sep. 1, 2021, 20230010510 A1.
U.S. Appl. No. 17/683,598, filed Mar. 1, 2022, 20220313987 A1.
U.S. Appl. No. 17/710,570, filed Mar. 31, 2022.
U.S. Appl. No. 18/186,927, filed Mar. 20, 2023.

| contact | stim. | rtn. |
|---|---|---|
| 112-1 | | |
| 112-2 | X | |
| 112-3 | | |
| 112-4 | | |
| 112-5 | | |
| 113-1 | | X |
| 113-2 | | X |

*FIG. 22A*

| contact | stim. | rtn. |
|---|---|---|
| 112-1 | X | |
| 112-2 | X | |
| 112-3 | | |
| 112-4 | | |
| 112-5 | | |
| 113-1 | | X |
| 113-2 | | X |

*FIG. 22B*

ELECTRODE LEADS HAVING MULTI-APPLICATION HELICAL NERVE CUFFS AND ASSOCIATED SYSTEMS AND METHODS

CROSS-REFERENCE TO RELATED APPLICATION

This application claims the benefit of U.S. Provisional Application No. 63/220,007, filed Jul. 9, 2021, and entitled "Parallel Electrode Helical Cuff Configurations," which is incorporated herein by reference.

BACKGROUND OF THE INVENTIONS

1. Field of Inventions

The present inventions relate generally to the treatment of obstructive sleep apnea by stimulating the hypoglossal nerve.

2. Description of the Related Art

Obstructive sleep apnea (OSA) is a highly prevalent sleep disorder that is caused by the collapse of or increase in the resistance of the pharyngeal airway, often resulting from tongue obstruction. The obstruction of the upper airway is mainly caused by reduced genioglossus muscle activity during the deeper states of non-rapid eye movement (NREM) sleep. In some OSA patients, obstruction occurs predominantly during rapid eye movement (REM) sleep. This is known as REM OSA and has different cardiometabolic and neurocognitive risks. Obstruction of the upper airway causes breathing to pause during sleep. Cessation of breathing, in turn, causes a decrease in the blood oxygen saturation level, which is eventually corrected when the person wakes up and resumes breathing. The long-term effects of OSA include, but are not limited to, high blood pressure, heart failure, strokes, diabetes, headaches, and general daytime sleepiness and memory loss.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of electrically conductive contacts on the cuff body, that is positioned around the HGN trunk. The HGN trunk nerve cuff may be configured in such a manner that it can be used to selectively stimulate nerve fascicles which innervate muscles that extend the tongue, while avoiding other nerve fascicles, with what is predominantly radial vector stimulation. For example, the contacts may be axially aligned and circumferentially spaced around the perimeter of the HGN trunk. In other instances, a nerve cuff is placed on the branch of the HGN that is responsible for protruding the tongue (hereafter "HGN genioglossus muscle branch" or "HGN GM branch"). A smaller diameter cuff with two or three axially spaced contacts may be used at the HGN GM branch because the nerve fascicles within this branch generally innervate the specific tongue protrusor muscle, but not other muscles. Put another way, the entire HGN GM branch is stimulated with what is predominantly axial vector stimulation. Exemplary nerve cuffs are illustrated and described in U.S. Pat. Pub. Nos. 2018/0318577A1, 2018/0318578A1, 2019/0060646A1 and 2019/0282805, which are incorporated herein by reference in their entirety.

SUMMARY

The present inventors have determined that conventional nerve cuffs are susceptible to improvement. In particular, the present inventors have determined that providing different nerve cuffs for the HGN trunk and HGN GM branch is not cost-effective because each nerve cuff must be separately developed and qualified, and then undergo successful clinical trials and regulatory approvals. One proposed solution to this problem in the art is to employ a helical nerve cuff that can be placed on differently sized nerve structures. The present inventors have determined that conventional helical nerve cuffs are susceptible to improvement. For example, they do not facilitate selective fascicle stimulation and, accordingly, are less than optimal for use on both the HGN trunk and the HGN GM branch.

An electrode lead in accordance with at least one of the present inventions includes an elongate lead body and a nerve cuff. The nerve cuff may include a biologically compatible, elastic, electrically insulative cuff body affixed to the distal end of the lead body, the cuff body being configured to be disposed around a nerve, having a pre-set furled helical state that defines an inner lumen, being movable to an unfurled state, and defining a length and a width in the unfurled state that is greater than the length. A plurality of electrically conductive contacts may be carried by the cuff body and spaced from one another in the width direction. A plurality of electrical conductors may be electrically connected to the electrically conductive contacts and extend through the lead body to the proximal end of the lead body. The present inventions also include systems with an implantable pulse generator or other implantable stimulation device in combination with such an electrode lead.

An electrode lead in accordance with at least one of the present inventions includes an elongate lead body and a nerve cuff. The nerve cuff may include a biologically compatible, elastic, electrically insulative cuff body affixed to the distal end of the lead body, the cuff body being configured to be disposed around a nerve, having a pre-set furled helical state that defines an inner lumen, being movable to an unfurled state, and defining a length and a width in the unfurled state that is greater than the length. First and second relatively wide electrically conductive contacts may be carried by the cuff body that are spaced from one another in the length direction and that extend in the width direction to such an extent that they extend completely around the cuff body inner lumen when the cuff body is in the pre-set furled shape. A plurality of relatively narrow electrically conductive contacts may be carried by the cuff body that are spaced from one another in the width direction and are located between the first and second relatively wide electrically conductive contacts. A plurality of electrical conductors may be electrically connected to the electrically conductive contacts and extend through the lead body to the proximal end of the lead body. The present inventions also include systems with an implantable pulse generator or other implantable stimulation device in combination with such an electrode lead.

A method in accordance with at least one of the present inventions includes the steps of placing a helical nerve cuff of an electrode lead on the hypoglossal nerve (HGN) that is configured for placement on either one of the HGN trunk and the branch of the HGN that is responsible for protruding the tongue (HGN GM branch), applying stimulation energy to the HGN trunk with the helical nerve cuff in instances where the nerve cuff is on the HGN trunk, and applying stimulation energy to the HGN GM branch with the helical nerve cuff in instances where the nerve cuff is on the HGN GM branch.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
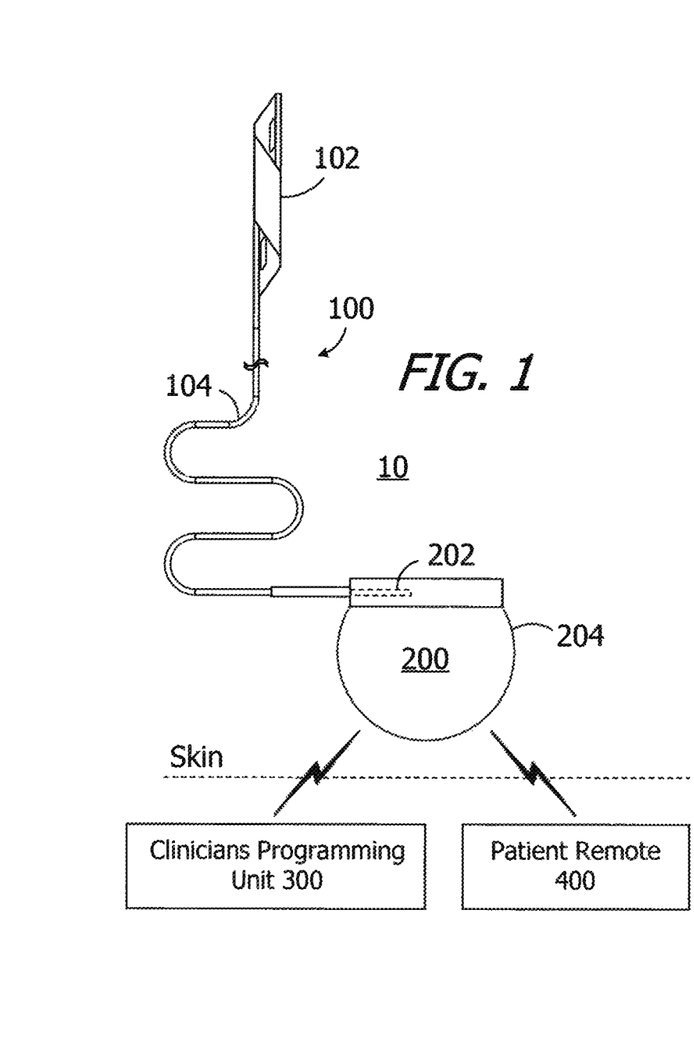
FIG. 1 is a plan view of a stimulation system in accordance with one embodiment of a present invention.
Figure 2:
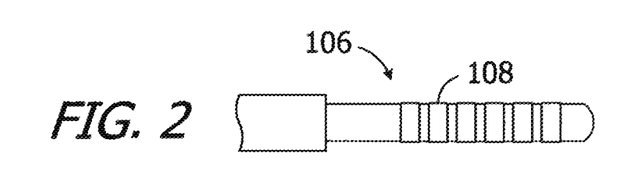
FIG. 2 is a plan view of a portion of the stimulation system illustrated in FIG. 1.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and an IPG charger (not shown) may also be provided in some instances. The exemplary electrode lead 100 includes a nerve cuff 102 and a lead body 104 that couples the nerve cuff 102 to the IPG 200 by way of lead connector 106, with a plurality of contacts 108, on the proximal end of the lead body 104 and a corresponding connector receptacle 202 on the IPG 200. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Figure 3:
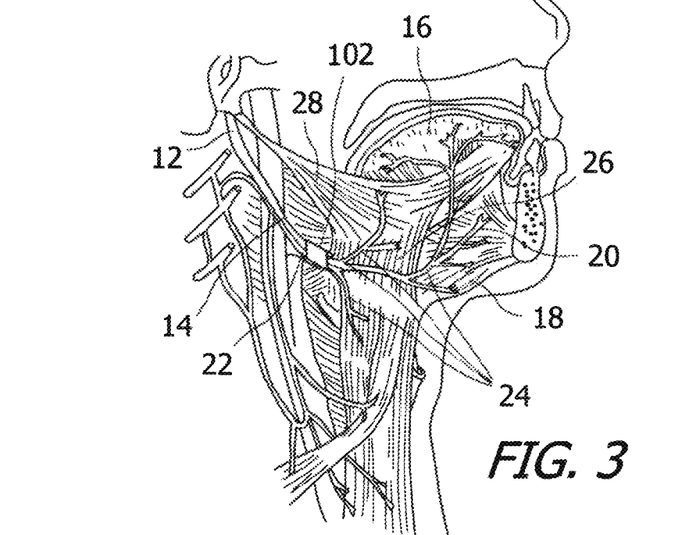
FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.
Figure 4:
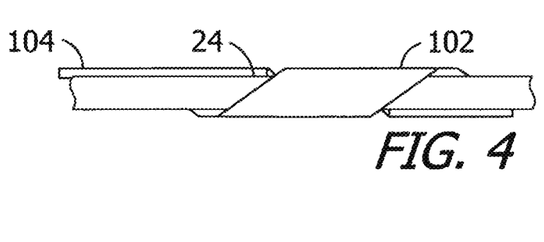
FIG. 4 is a side view showing the nerve cuff illustrated in FIG. 1 on the HGN GM branch.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

Figures 5, 6, 7, 8:
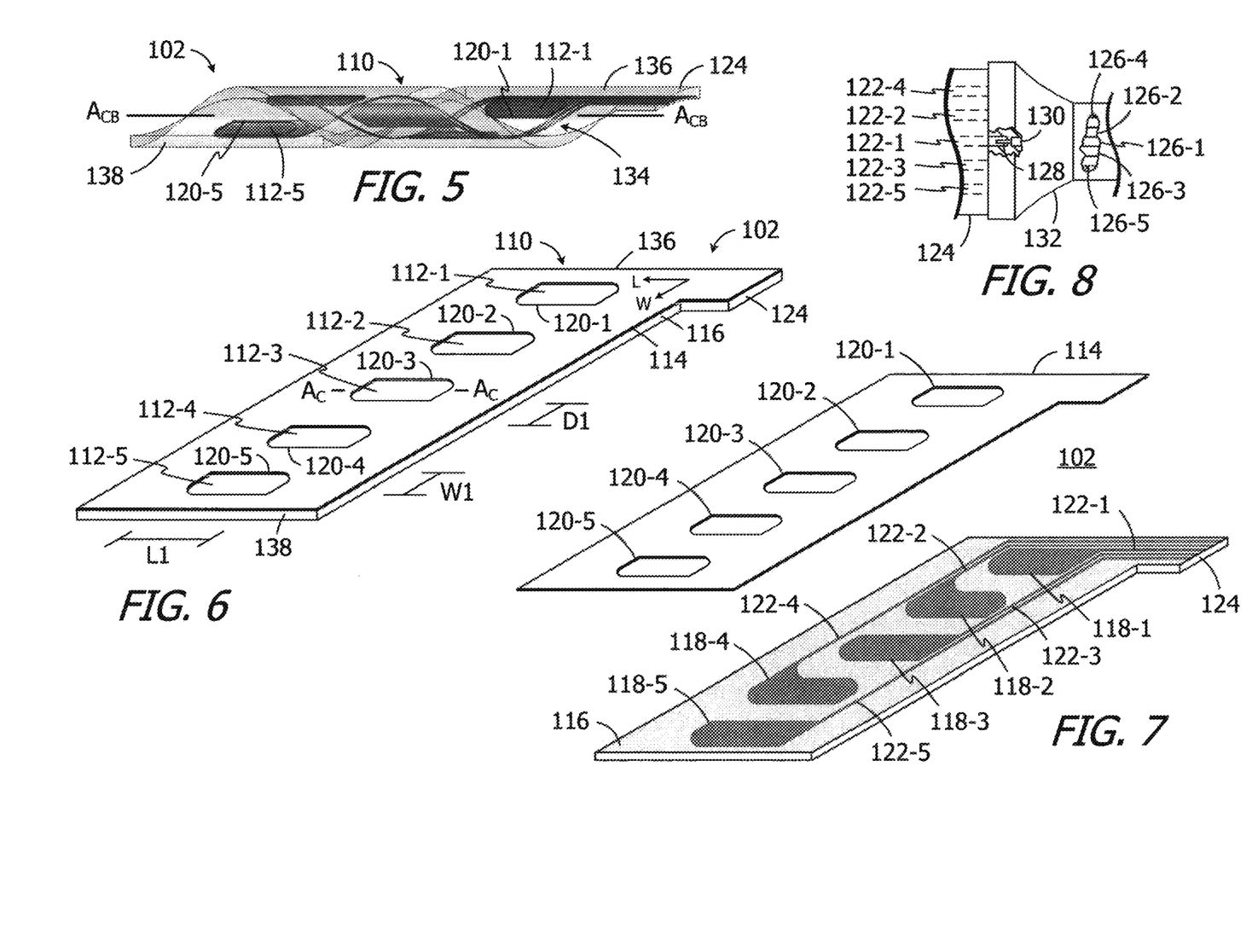
FIG. 5 is a side view of the nerve cuff illustrated in FIG. 1 in a pre-shaped furled state.
FIG. 6 is a perspective view of the nerve cuff illustrated in FIG. 1 in an unfurled state.
FIG. 7 is an exploded perspective view of the nerve cuff illustrated in FIG. 1 in the unfurled state.
FIG. 8 is a side view of a portion of the electrode lead illustrated in FIG. 1.

The exemplary nerve cuff 102 is shown in various furled states in FIGS. 5 and 9-12B that the nerve cuff will be in when it wraps around an HGN trunk 14 or HGN GM branch 24, and is shown in a flattened, unfurled state in FIGS. 6 and 7. The exemplary nerve cuff 102 is helical in shape when in a furled state. In the illustrated implementation, the nerve cuff 102 is pre-set (or "pre-shaped") to the furled (or "curled") state illustrated in FIGS. 5 and 9-10B, and an external force may be used to partially or completely unfurl the nerve cuff 102. The nerve cuff 102 will return to the pre-shaped helical furled state when the force is removed and, as discussed below, may assume one of the furled states illustrated in FIGS. 5 and 9-12B depending on the size of the HGN trunk or HGN branch that the nerve cuff 102 is placed around.

Referring first to FIGS. 5 and 6, the nerve cuff 102 includes a cuff body 110 and a plurality of electrically conductive contacts 112-1 to 112-5 (collectively "electrically conductive contacts 112") on the cuff body 110. The cuff body 110 defines a central axis $A_{CB}$ when in the furled, helical state (FIG. 5) and defines a length and a width that is greater than the length when in the unfurled state (FIG. 6). The cuff body central axis $A_{CB}$ will also be coaxial with the nerve central axis $A_N$ as is discussed below with reference to FIGS. 9-12B. The electrically conductive contacts 112 extend in the length direction, are spaced from one another in the width direction, and each define a longitudinal axis $A_C$ that is parallel to cuff body central axis $A_{CB}$ and, accordingly, is parallel to the nerve central axis $A_N$ as is also discussed below with reference to FIGS. 9-12B. Although the number may increase or decrease in the context of other nerve applications, at least five electrically conductive contacts 112 may be spaced from one another in the width direction. With respect to shape, and although the present inventions are not so limited, the contacts 112 are in the shape of rectangles with two or more curved corners (i.e., are "generally rectangular") and the length is greater than the width.

The contacts 112-1 to 112-5 may be of any suitable construction. In the illustrated implementation, the cuff body 110 includes a front layer 114 that will face the HGN trunk or branch and a rear layer 116 that will face away from the HGN trunk or branch. Five conductive members 118-1 to 118-5 are located between the front layer 114 and rear layer 116. The conductive members 118-1 to 118-5 are exposed by way of openings 120-1 to 120-5 in the cuff body front layer 114. The openings 120-1 to 120-5 extend from the outer surface of the front layer 114 to the associated conductive members 118-1 to 118-5, and the exposed portions of the conductive members 118-1 to 118-5 define the contacts 112-1 to 114-5.

The contacts 112-1 to 112-5 in the illustrated embodiment may be electrically connected to the plurality of contacts 108 on the lead connector 106 (FIG. 2) by conductive traces 122-1 to 122-5, which extend along the rear layer 116 from each of the conductive members 118-1 to 118-5 to a tab 124, and wires 126-1 to 126-5 that extend through the lead body 104. Each wire 126-1 to 126-5 includes a conductor 128 and an insulator 130. The conductors 128 may be connected to the ends of the traces 122-1 to 122-5 on the tab 124 by welding or other suitable processes in an area thereafter covered by an overmold 132, as shown in FIG. 8.

Figure 9:
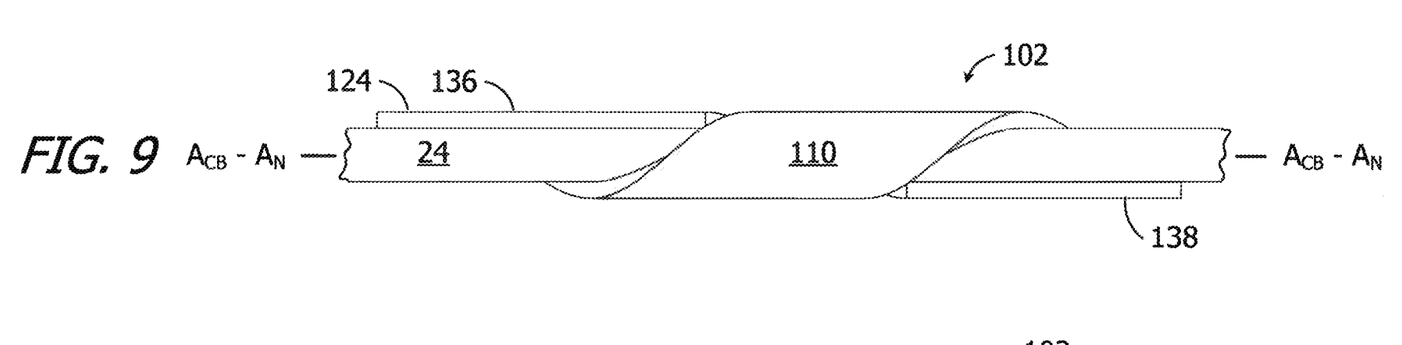
FIG. 9 is a side view of the nerve cuff illustrated in FIG. 1 on an HGN branch and in the pre-shaped furled state.
Figure 10A:
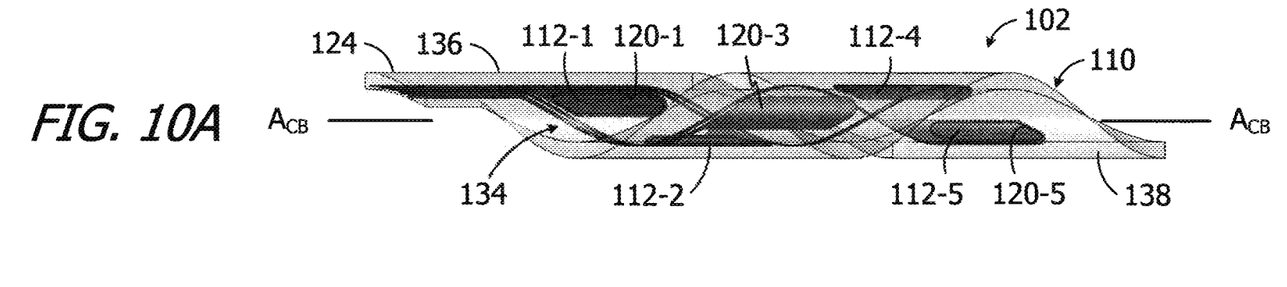
FIG. 10A is a side view of the nerve cuff illustrated in FIG. 9 with the HGN branch removed.
Figure 10B:
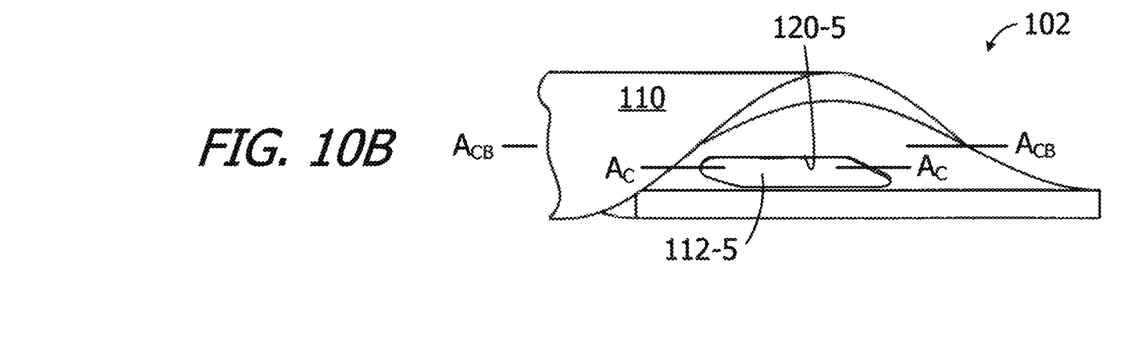
FIG. 10B is an enlarged view of a portion of FIG. 10A.
Figure 11:
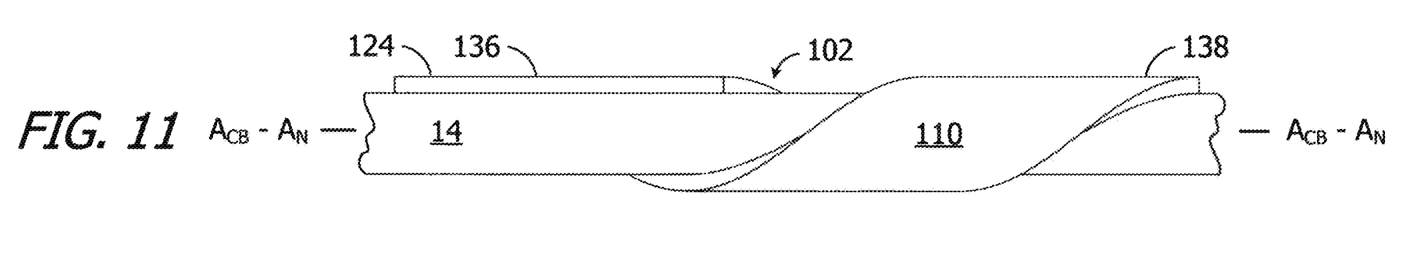
FIG. 11 is a side view of the nerve cuff illustrated in FIG. 1 on an HGN trunk and in an expanded and less tightly furled state.
Figure 12A:
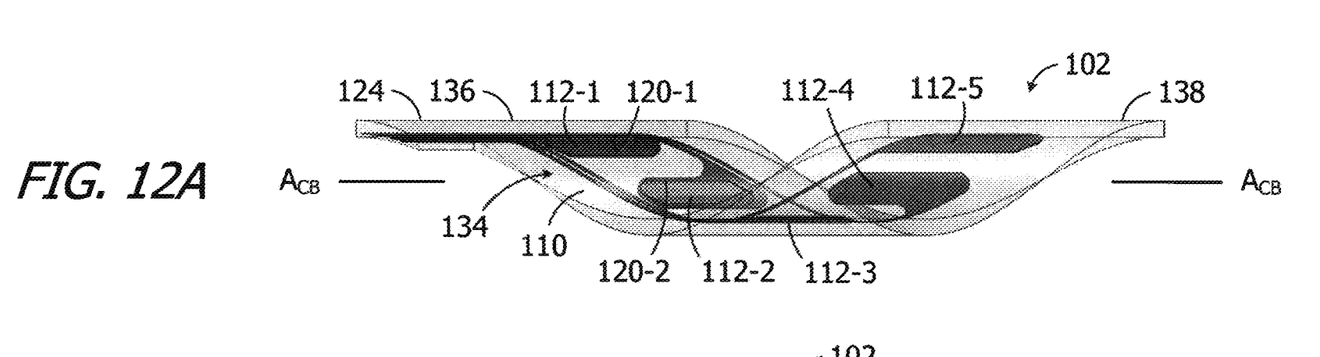
FIG. 12A is a side view of the nerve cuff illustrated in FIG. 11 with the HGN trunk removed.
Figure 12B:
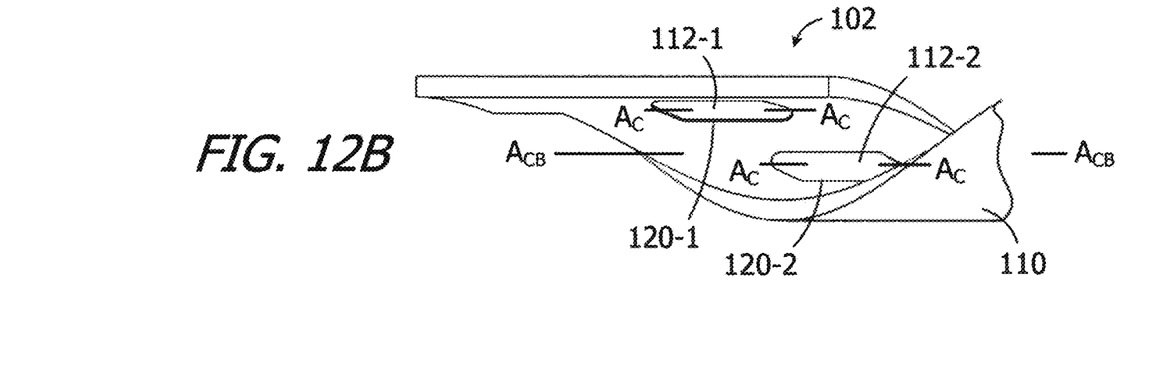
FIG. 12B is an enlarged view of a portion of FIG. 12A.

The exemplary cuff body 110 may be formed from any suitable material. Such materials may be biologically compatible, electrically insulative, elastic and capable of functioning in the manner described herein. By way of example, but not limitation, suitable cuff body materials include silicone, polyurethane and liquid crystal polymers that are pliable enough to allow a clinician to unfurl the cuff body 110 (and nerve cuff 102) and place the nerve cuff around the HGN trunk (or HGN GM branch). The exemplary materials should also be resilient enough to cause the nerve cuff return to the pre-shaped furled state illustrated in FIGS. 9-10B when the force is removed, yet flexible enough to allow the cuff body 110 (and nerve cuff 102) to instead assume the slightly larger, expanded and less tightly furled states, such as the state illustrated in FIGS. 11-12B. To that end, the furled cuff body 110 defines an inner lumen 134, in which the nerve will be located after the nerve cuff 102 wraps around the nerve, as well as lateral ends 136 and 138. Comparing the state illustrated in FIGS. 9-10B to the state illustrated in FIGS. 11-12B, the inner lumen 134 is slightly larger and the lateral end 138 is offset around the perimeter of the nerve from its pre-shaped furled state because the helical cuff body 110 unwinds as the diameter of the helix increases. For example, the inner lumen 134 in FIGS. 9-10B is sized to accommodate an HGN structure that has a diameter of about 2.5 mm (e.g., the HGN GM branch 24), while the inner lumen 134 in FIGS. 11-12B is sized to accommodate an HGN structure that has a diameter of about 4.0 mm (e.g., the HGN trunk 14). In either state, there is sufficient contact coverage around the circumference of the associated nerve to activate the desired portion of the nerve trunk or branch. The cuff body 110 (and nerve cuff 102) can also accommodate an HGN structures that have a diameter in between the state illustrated in FIGS. 9-10B and the state illustrated in FIGS. 11-12B such as, for example, when the HGN GM branch 24 in a swollen state where the diameter is about 3.0 mm. The ability to assume slightly larger, expanded and less tightly furled states, in addition to the smaller fully furled state, allows the same nerve cuff 102 to accommodate either of the larger HGN trunk 14 or a smaller HGN branch 24. The ability to assume slightly larger, expanded furled states also allows the nerve cuff to accommodate nerve swelling that may occur post-surgery and to self-adjust to a smaller state when the swelling subsides.

It should be noted here that in the state illustrated in FIGS. 9-10B, the state illustrated in FIGS. 11-12B, and states therebetween, the longitudinal axis $A_C$ of each of the electrically conductive contacts 112-1 to 112-5 is parallel to cuff body central axis $A_{CB}$ and, accordingly, is parallel to the nerve central axis $A_N$ when the cuff is on a nerve such as the HGN trunk or a smaller HGN branch. The rectangular shape of the electrically conductive contacts 112-1 to 112-5, combined with parallel orientation of the longitudinal axes $A_C$ thereof, results in contacts that have surface areas sufficient to reduce the likelihood that current concentration will result in nerve damage, while at the same time providing contacts that are sufficiently spaced from one another around the circumference of the nerve to enable selective activation of the fascicles. Such selective activation is especially useful when the nerve cuff 102 (or the nerve cuff 102a discussed below) is on the larger HGN trunk 14.

The dimensions of the present nerve cuffs, including the various elements thereof, may by any dimensions that result in the nerve cuffs functioning as intended. With respect to the dimensions of the cuff body 110 of the exemplary nerve cuff 102, and referring to FIG. 6, the cuff body is about 1.0 inches wide and about 0.5 inches long. As used herein in the context of dimensions, the word "about" means ±10-20%. The contacts 112-1 to 112-5 are same size in the illustrated implementation, but may be different sizes in other implementations. Referring to FIG. 6, the width W1 of the contacts 112-1 to 112-5 is about 0.05 inches, the length L1 is about 0.2 inches, and the distance D1 between adjacent contacts 112 is about 0.05 inches. The distance D2 may also be increased or decreased as desired to accomplish various stimulation objectives. The conductive members 118-1 to 118-5 and the traces 122-1 to 122-5 may be formed from materials such as, for example, platinum-iridium, platinum and stainless steel and by processes such as, for example, deposition onto the cuff body and etching remotely and subsequent transfer onto the cuff body. Appropriately shaped conductive members may also be manufactured, placed onto the rear layer 116 and connected to wires instead of the traces 122.

Figure 13:
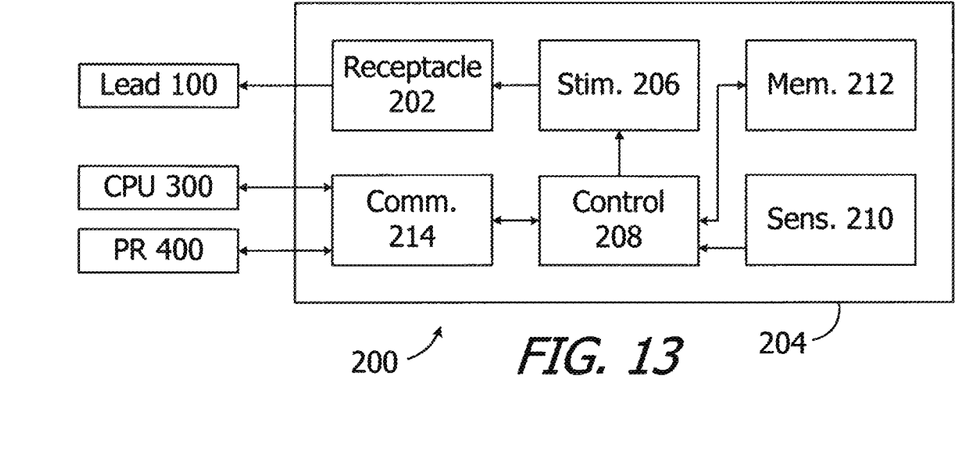
FIG. 13 is a block diagram of the stimulation system illustrated in FIG. 1.

Turning to FIG. 13, the exemplary IPG 200 includes the aforementioned receptacle 202, a hermetically sealed outer case 204, and various circuitry (e.g., stimulation circuitry 206, control circuitry 208, sensing circuitry 210, memory 212, and communication circuitry 214) that is located within the outer case 204. The outer case 204 may be formed from an electrically conductive, biocompatible material such as titanium. The stimulation circuitry 206, which is coupled to the contacts 112-1 to 112-5 by way of the connector 106, receptacle 202, wires 126-1 to 126-5 and conductive traces 122-1 to 122-5, is configured to deliver stimulation energy to the HGN. The control circuitry 208 controls when and for how long the stimulation circuitry 206 applies stimulation, the intensity of the stimulation, the mode of stimulation (i.e., monopolar, bipolar or tripolar), and the particular contacts that are used in the stimulation. In the monopolar stimulation, at least a portion of the outer case 204 functions as a return electrode in the electrical circuit that also includes one or more of the contacts 112-1 to 112-5. In bipolar stimulation, the outer case 204 is not part of the electrical circuit and current instead flows from one of the contacts 112-1 to 112-5 to one of the other contacts 112-1 to 112-5. In tripolar stimulation, the outer case 204 is not part of the electrical circuit and current flows from one or more of the contacts 112-1 to 112-5 to more than one of the other contacts 112-1 to 112-5. The contacts to which the current flows form part of the return path for the stimulation energy, as do the associated wires connected thereto. Depending on the size of the nerve on which the nerve cuff 102 is placed and the contacts that are employed, stimulation may also be predominantly axial vector stimulation or a hybrid of axial vector and radial vector.

The sensing circuitry 210 in the illustrated embodiment may be connected to one or more sensors (not shown) that are contained within the outer case 204. Alternatively, or in addition, the sensors may be affixed to the exterior of the outer case 204 or positioned at a remote site within the body and coupled to the IPG 200 with a connecting lead. The sensing circuitry 210 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 212 stores data gathered by the sensing circuitry 210, programming instructions and stimulation parameters. The control circuitry 208 analyzes the sensed data to determine when stimulation should be delivered. The communication circuitry 214 is configured to wirelessly communicates with the clinician's programming unit 300 and patient remote 400 using radio frequency signals.

The control circuitry 208 may apply stimulation energy to either the HGN trunk or an HGN branch (e.g. the HGN GM branch) in various stimulation methodologies by way of the cuff 102 when the patient is in the inspiratory phase of respiration, and other conditions for stimulation are met, thereby causing anterior displacement of the tongue to keep the upper airway unobstructed. The control circuitry 208 causes the stimulation circuitry 206 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

Figure 14A:
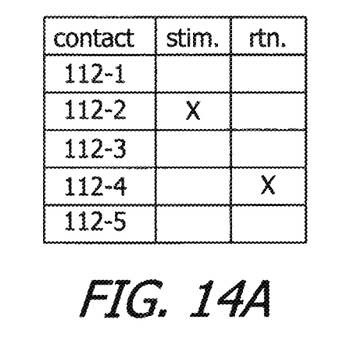
FIG. 14A is a table showing a stimulation methodology in accordance with one embodiment of a present invention.

Any combination of contacts and stimulation mode may be employed so long as the desired therapeutic result is achieved. One exemplary stimulation methodology is illustrated in FIG. 14A. Here, the nerve cuff 102 is positioned on an HGN branch (such as the HGN GM branch 14) and is in the pre-shaped furled state illustrated in FIGS. 9-10B. The IPG 200 supplies stimulation energy to contact 112-2 and contact 112-4 forms part of the return path for the stimulation energy. In other words, contact 112-2 functions as a cathode and contact 112-4 functions as an anode. The stimulation current has an axial vector and radial vector along the HGN branch and, as a result, the entire HGN branch is stimulated.

Figure 14B:
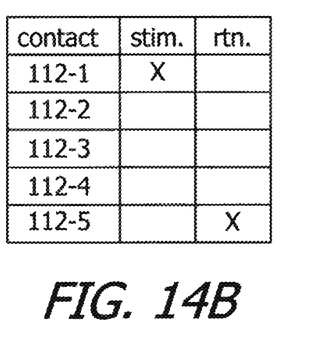
FIG. 14B is a table showing a stimulation methodology in accordance with one embodiment of a present invention.

Another exemplary stimulation methodology is illustrated in FIG. 14B. Here, the nerve cuff 102 is in an expanded state and is positioned on the HGN trunk 14 in the manner described above with reference to FIGS. 11-12B. The IPG 200 supplies stimulation energy to contact 112-1 and contact 112-5 forms part of the return path for the stimulation energy. In other words, contact 112-1 functions as a cathode and contact 112-5 functions as an anode. The stimulation current has a primarily axial vector along the HGN trunk and, as a result, the fascicle(s) adjacent to that portion of the HGN trunk are stimulated.

Figure 14C:
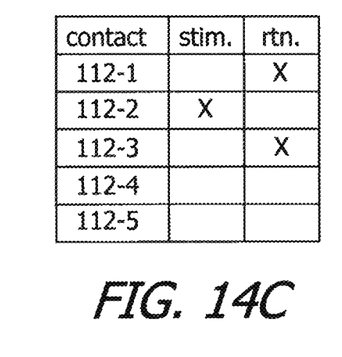
FIG. 14C is a table showing a stimulation methodology in accordance with one embodiment of a present invention.

In the exemplary stimulation methodology is illustrated in FIG. 14C, the nerve cuff 102 is positioned is in an expanded state and is positioned on the HGN trunk 14 in the manner described above with reference to FIGS. 11-12B. The IPG 200 supplies stimulation energy to contact 112-2 and contacts 112-3 and 112-1 form part of the return path for the stimulation energy. In other words, contact 112-2 functions as a cathode and contacts 112-3 and 112-1 function as anodes. The stimulation current has an axial vector and a radial vector.

Figure 15:
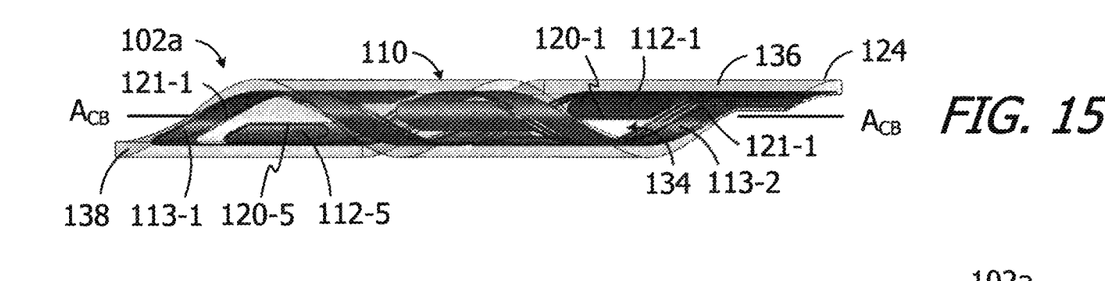
FIG. 15 is a side view of a nerve cuff in accordance with one embodiment of a present invention in a pre-shaped furled state.
Figure 16:
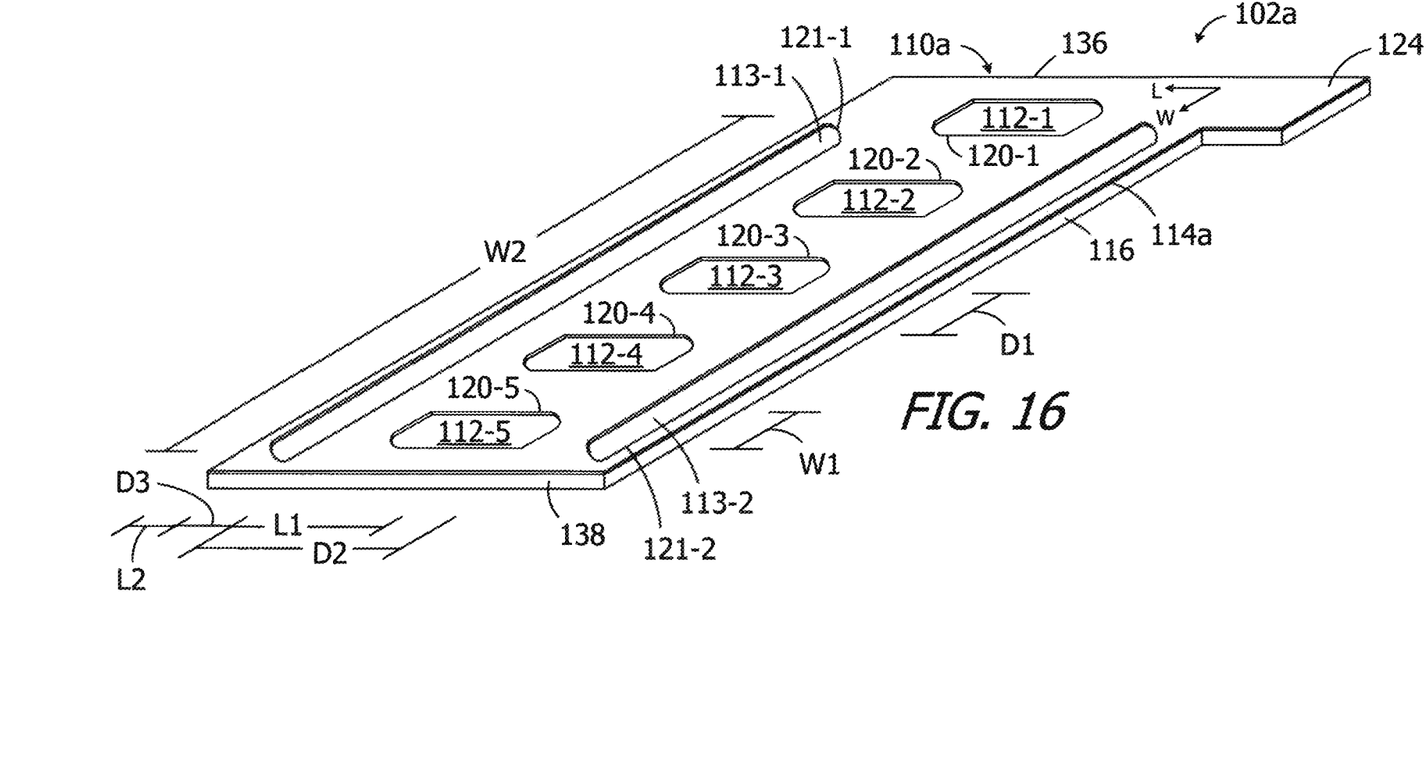
FIG. 16 is a perspective view of the nerve cuff illustrated in FIG. 15 in an unfurled state.
Figure 17:
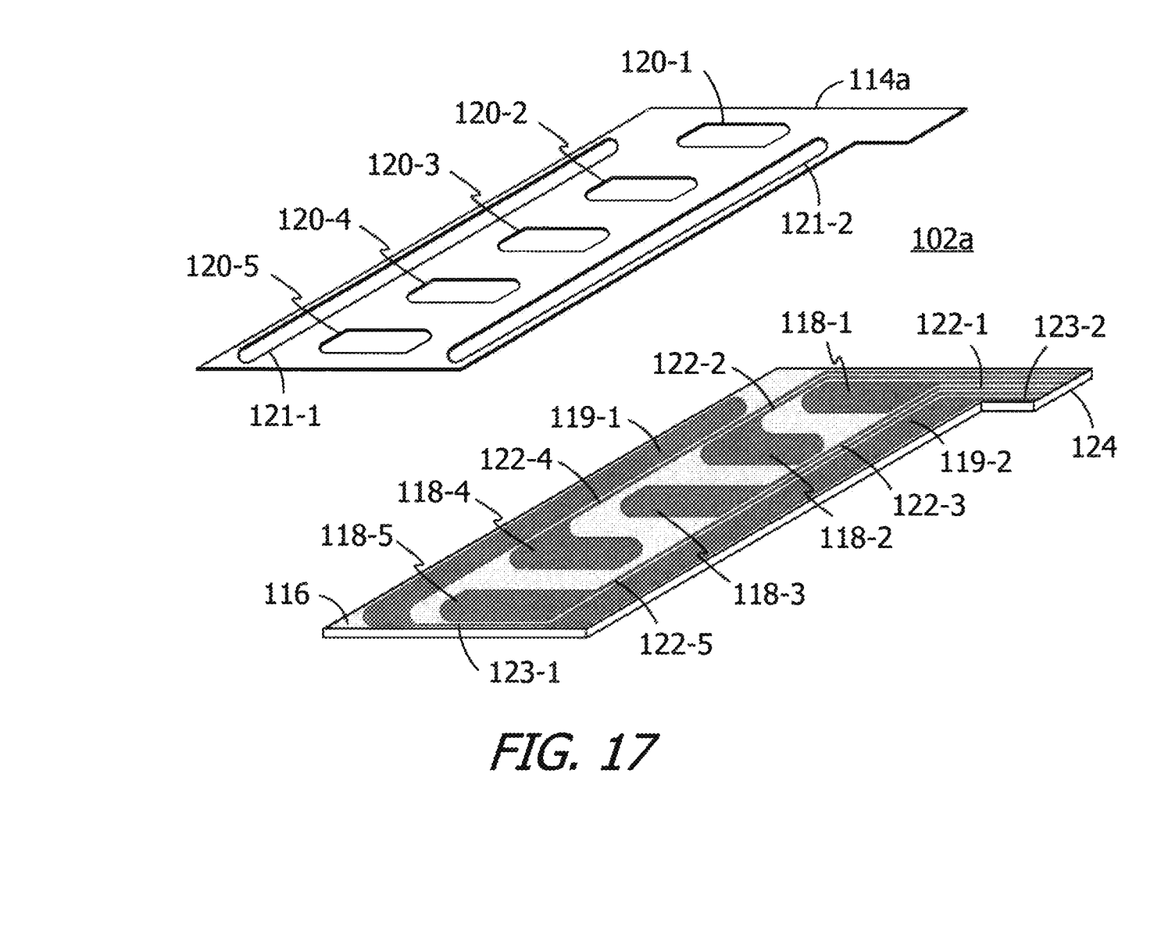
FIG. 17 is an exploded perspective view of the nerve cuff illustrated in FIG. 15 in the unfurled state.

Another exemplary nerve cuff is generally represented by reference numeral 102a in FIGS. 15-17. The exemplary nerve cuff 102a, which may be combined with a lead body to form an electrode lead in the manner described above with reference to FIG. 1, is substantially similar to nerve cuff 102 and similar elements are represented by similar reference numerals. The descriptions above of the elements in the nerve cuff 102 are applicable to the nerve cuff 102a. Here, however, the nerve cuff 102a includes first and second relatively wide electrically conductive contacts (or "relatively wide contacts") 113-1 and 113-2 on the cuff body 110a that extend in the width direction and are spaced from one another in the length direction. The contacts 112-1 to 112-5, which are relatively narrow as compared to the contacts 113-1 and 113-2, are located between the relatively wide contacts 113-1 and 113-2. As used herein, "relatively wide" structures are structures that are longer in the width direction than structures that are referred to as "relatively narrow" and "relatively narrow" structures are structures that are shorter in the width direction than structures that are referred to as "relatively wide." In the implementation illustrated in FIGS. 15 and 16, the relatively narrow contacts 112-1 to 112-5 are centered relative to the contacts 113-1 and 113-2 and are aligned with one another in the length direction. In other implementations, the relatively narrow contacts 112-1 to 112-5 may be non-centered relative to the relatively wide contacts 113-1 and 113-2 and/or offset from one another in the length direction. In other implementations, contacts 113-1 and 113-2 may be segmented or split into sections and connected, for example, by trace or wire. With respect to shape, and although the present inventions are not so limited, the relatively wide contacts 113-1 and 113-2 are in the shape of rectangles with semi-circular ends.

Like the contacts 112-1 to 112-5, the contacts 113-1 and 113-2 may be of any suitable construction. In the illustrated implementation, and referring more specifically to FIG. 17, the contacts 113-1 and 113-2 are formed by conductive members 119-1 and 119-2 that are located between the front layer 114a and rear layer 116 of the cuff body 110a as well as by openings 121-1 and 121-2 that extend through the front layer 114a to expose the portions of the conductive members 119-1 and 119-2 that define the contacts 113-1 and 113-2. The contacts 113-1 and 113-2 in the illustrated embodiment may be electrically connected to a contact on a lead connector (e.g., a modified version of the connector 106 in FIG. 2) by a conductive trace 123-1 that extends from the member 119-1 to the conductive member 119-2, a conductive trace 123-2 that extends from the conductive member 119-2 to the tab 124, and a wire that is connected to the end of the conductive trace 123-2 in the manner described above with reference to FIG. 8. In other implementations, the conductive trace 123-1 may be omitted and the conductive members 119-1 and 119-2 may be separately and individually connected to the lead connector. The conductive members 119 and traces 123 may be formed by the same methods and from the same materials as the conductive members 118 and the traces 122.

Figure 18:
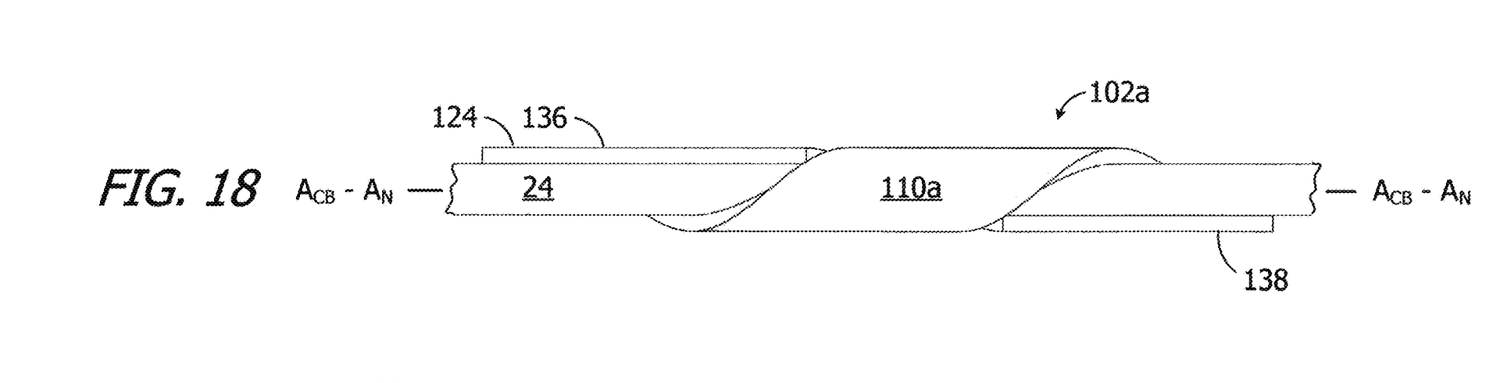
FIG. 18 is a side view of the nerve cuff illustrated in FIG. 15 on an HGN branch and in the pre-shaped furled state.
Figure 19A:
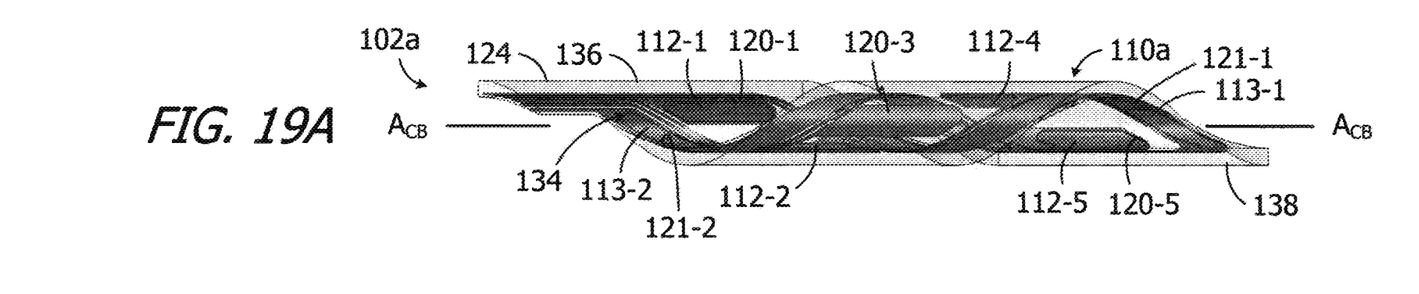
FIG. 19A is a side view of the nerve cuff illustrated in FIG. 18 with the HGN branch removed.
Figure 19B:
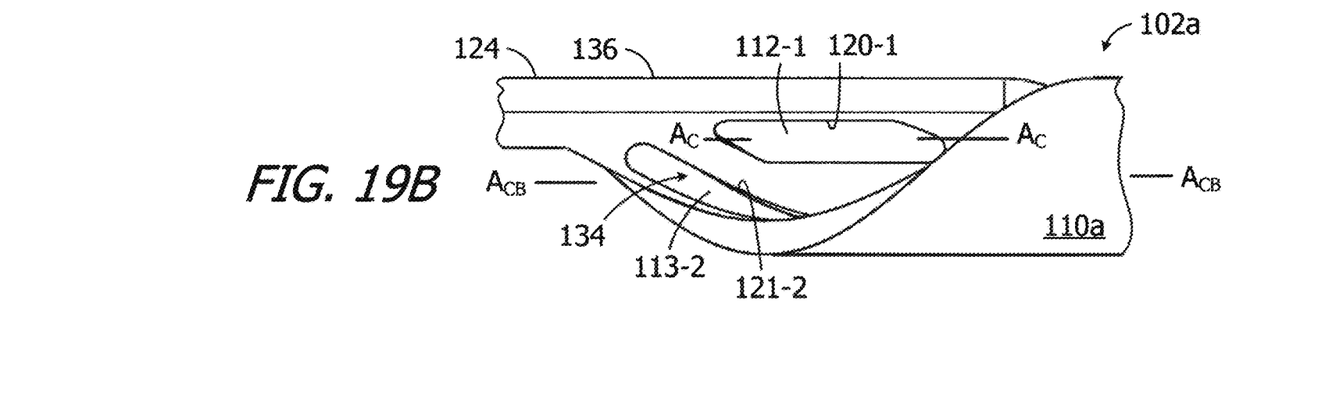
FIG. 19B is an enlarged view of a portion of FIG. 19A.
Figures 20, 21A:
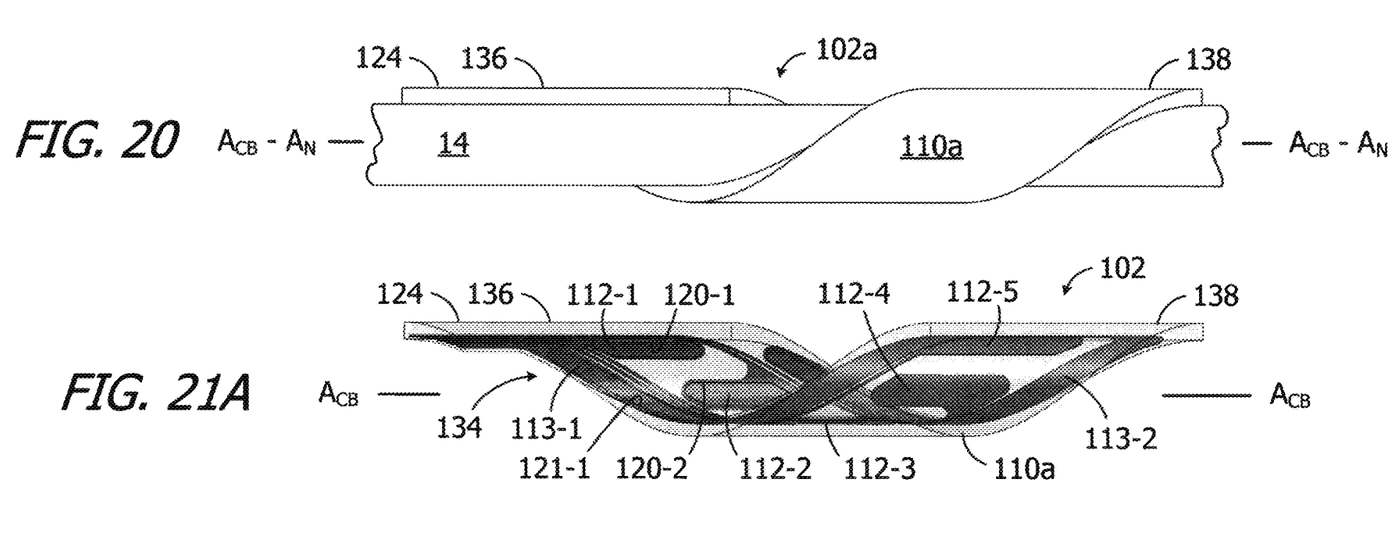
FIG. 20 is a side view of the nerve cuff illustrated in FIG. 15 on an HGN trunk and in an expanded and less tightly furled state.
FIG. 21A is a side view of the nerve cuff illustrated in FIG. 20 with the HGN trunk removed.
Figure 21B:
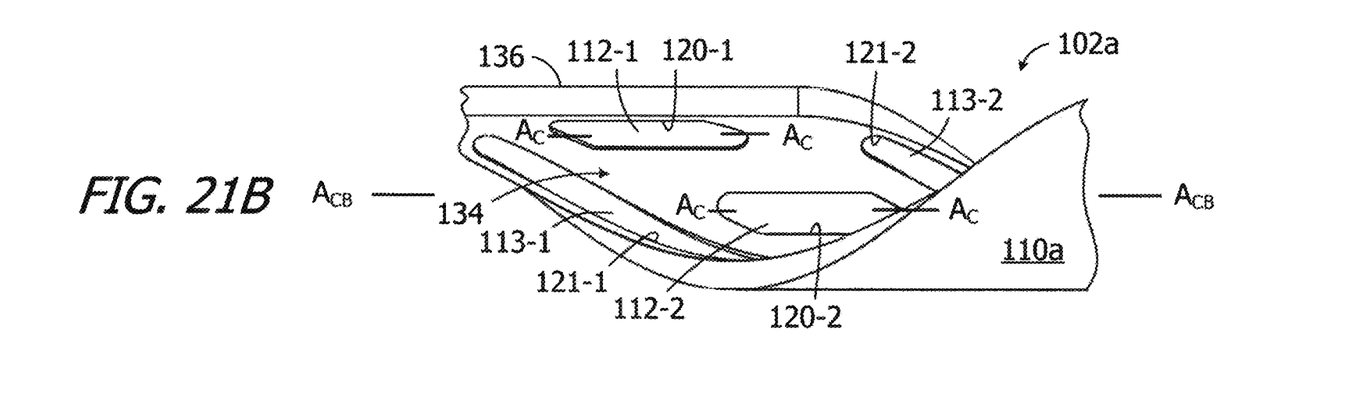
FIG. 21B is an enlarged view of a portion of FIG. 21A.

The exemplary nerve cuff 102a is shown in its pre-shaped furled state in FIGS. 18-19B and in a slightly larger, expanded and less tightly furled states, such as the state illustrated in FIGS. 20-21B. Comparing the state of the nerve cuff 102a in FIGS. 18-19B to the state illustrated in FIGS. 20-21, the inner lumen 134 is slightly larger and the lateral end 138 is offset around the perimeter of the nerve from its pre-shaped furled state because the helical cuff body 110a unwinds as the diameter of the helix increases. The inner lumen 134 in FIGS. 18-19B is sized to accommodate an HGN structure that has a diameter of about 2.5 mm (e.g., the HGN GM branch 24), while the inner lumen 134 in FIGS. 20-21B is sized to accommodate an HGN structure that has a diameter of about 4.0 mm (e.g., the HGN trunk 14). The cuff body 110 (and nerve cuff 102) can also accommodate an HGN structures that have a diameter in between the state illustrated in FIGS. 18-19B and the state illustrated in FIGS. 20-21B. Here too, in any of these states, the longitudinal axis $A_C$ of each of the electrically conductive contacts 112-1 to 112-5 is parallel to cuff body central axis $A_{CB}$ and, accordingly, is parallel to the nerve central axis $A_N$ when the cuff is on a nerve such as the HGN trunk or a smaller HGN branch. The electrically conductive contacts 113-1 and 113-2, on the other hand, extend helically around the cuff body central axis $A_{CB}$ and around the nerve central axis $A_N$ when the nerve cuff 102a is on a nerve.

Figure 22A:
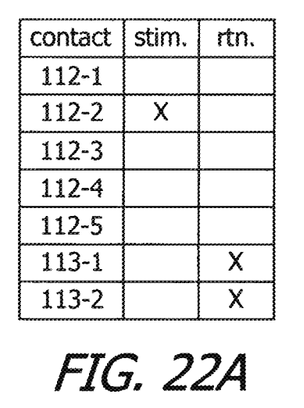
FIG. 22A is a table showing a stimulation methodology in accordance with one embodiment of a present invention.

One exemplary stimulation methodology is illustrated in FIG. 22A. Here, the nerve cuff 102a is positioned on an HGN branch 24 (such as the HGN GM branch) and is in the pre-shaped furled state illustrated in FIGS. 18-19B. The IPG 200 supplies stimulation energy to contact 112-2 and contacts 113-1 and 113-2 form part of the return path for the stimulation energy. In other words, contact 112-2 functions as a cathode and contacts 113-1 and 113-2 function as anodes. The stimulation field extends primarily from the contact 112-2 to the adjacent portions of the contacts 113-1 and 113-2 and has a primarily axial vector along the HGN trunk. The stimulation current has an axial vector along the HGN branch and, as a result, only the associated portion of the HGN branch is stimulated.

Figure 22B:
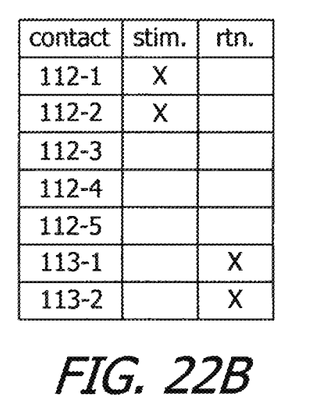
FIG. 22B is a table showing a stimulation methodology in accordance with one embodiment of a present invention.

Another exemplary stimulation methodology is illustrated in FIG. 22B. Here, the nerve cuff 102a is in an expanded state and is positioned on the HGN trunk 14 in the manner described above with reference to FIGS. 20-21B. The IPG 200 supplies stimulation energy to contacts 112-1 and 112-2 while contacts 113-1 and 113-2 form part of the return path for the stimulation energy. In other words, contacts 112-1 and 112-2 function as cathodes and contacts 113-1 and 113-2 function as anodes. The stimulation field extends primarily from the contacts 112-1 and 112-2 to the adjacent portions of the contacts 113-1 and 113-2 and has a primarily axial vector along the HGN trunk.

Although the inventions disclosed herein have been described in terms of the preferred embodiments above, numerous modifications and/or additions to the above-described preferred embodiments would be readily apparent to one skilled in the art. By way of example, but not limitation, the present inventions are applicable to other portions of the peripheral nervous system, such as the glossopharyngeal, vagus, and optic nerves, as well as other nerves, and present inventions include stimulating these nerves with the nerve cuffs disclosed herein. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An electrode lead, comprising:
   an elongate lead body having a proximal end and a distal end;
   a biologically compatible, elastic, electrically insulative cuff body affixed to the distal end of the lead body, the cuff body being configured to be disposed around a nerve, having a pre-set furled helical state that defines an inner lumen and a central axis, being movable to an unfurled state, and defining a length and a width in the unfurled state that is greater than the length;
   a plurality of generally rectangular electrically conductive contacts carried by the cuff body that are spaced from one another in the width direction, each electrically conductive contact defining a width, a length that is greater than the width, and a longitudinal axis that is parallel to cuff body central axis; and
   a plurality of electrical conductors that are electrically connected to the electrically conductive contacts and that extend through the lead body to the proximal end of the lead body.

2. An electrode lead as claimed in claim 1, wherein the plurality of electrically conductive contacts comprises at least five electrically conductive contacts.

3. An electrode lead as claimed in claim 1, wherein a plurality of lead connector terminals at the proximal end of the lead body that are connected to the plurality of electrical conductors.

4. An electrode lead, comprising:
   an elongate lead body having a proximal end and a distal end;
   a biologically compatible, elastic, electrically insulative cuff body affixed to the distal end of the lead body, the cuff body being configured to be disposed around a nerve, having a pre-set furled helical state that defines an inner lumen, being movable to an unfurled state, and having a length defining a length direction and a width in the unfurled state, that is greater than the length, defining a width direction;

first and second relatively wide electrically conductive contacts carried by the cuff body that are spaced from one another in the length direction and that extend in the width direction to such an extent that they each extend completely around the cuff body inner lumen when the cuff body is in the pre-set furled shape;

a plurality of relatively narrow electrically conductive contacts carried by the cuff body that are spaced from one another in the width direction and are located between the first and second relatively wide electrically conductive contacts; and a plurality of electrical conductors that are electrically connected to the electrically conductive contacts and that extend through the lead body to the proximal end of the lead body.

5. An electrode lead as claimed in claim 4, further comprising:
a plurality of lead connector terminals at the proximal end of the lead body that are connected to the plurality of electrical conductors.

6. An electrode lead as claimed in claim 4, wherein the first and second relatively wide electrically conductive contacts are the same length.

7. An electrode lead as claimed in claim 4, wherein the first and second relatively wide electrically conductive contacts are the only two relatively wide electrically conductive contacts.

8. An electrode lead as claimed in claim 4, wherein the first and second relatively wide electrically conductive contacts are parallel to one another.

9. An electrode lead as claimed in claim 4, wherein the relatively narrow electrically conductive contacts each define a width and a length that is greater than the width.

10. An electrode lead as claimed in claim 9, wherein the cuff body defines a central axis when in the furled, helical state; and
the relatively narrow electrically conductive contacts each define electrically conductive contacts each define a longitudinal axis that is parallel to cuff body central axis.

11. An electrode lead as claimed in claim 4, wherein the plurality of relatively narrow electrically conductive contacts comprises at least five relatively narrow electrically conductive contacts.

12. An electrode lead as claimed in claim 4, wherein all of the relatively narrow electrically conductive contacts are equidistant from the first and second relatively wide electrically conductive contacts.

13. A method, comprising:
placing a helical nerve cuff of an electrode lead as claimed in claim 1 on the hypoglossal nerve (HGN) trunk or on the branch of the HGN that is responsible for protruding the tongue (HGN GM branch);
applying stimulation energy to the HGN trunk with the helical nerve cuff in instances where the nerve cuff is on the HGN trunk; and
applying stimulation energy to the HGN GM branch with the helical nerve cuff in instances where the nerve cuff is on the HGN GM branch.

14. A method as claimed in claim 13, wherein
applying stimulation energy to the HGN GM branch with the helical nerve cuff comprises applying stimulation energy to the HGN GM branch with one electrically conductive contact and returning the stimulation energy with another one of the conductive contacts.

15. A method, comprising
placing a helical nerve cuff of an electrode lead as claimed in claim 7 on the hypoglossal nerve (HGN) trunk or on the branch of the HGN that is responsible for protruding the tongue (HGN GM branch);
applying stimulation energy to the HGN trunk with the helical nerve cuff in instances where the nerve cuff is on the HGN trunk; and
applying stimulation energy to the HGN GM branch with the helical nerve cuff in instances where the nerve cuff is on the HGN GM branch.

16. A method as claimed in claim 15, wherein
applying stimulation energy to the HGN GM branch with the nerve cuff comprises applying stimulation energy to the HGN GM branch with at least one of the relatively narrow electrically conductive contacts and returning the stimulation energy with at least one of the relatively wide electrically conductive contacts.

17. A method, comprising:
placing a helical nerve cuff of an electrode lead as claimed in claim 1 on a nerve; and
applying stimulation energy to the nerve with the helical nerve cuff.

18. A method as claimed in claim 17, wherein the helical nerve cuff is in a pre-set furled helical state on the nerve.

19. A method as claimed in claim 17, wherein the helical nerve cuff is in a partially unfurled helical state on the nerve.

* * * * *